(12) United States Patent
Dougherty et al.

(10) Patent No.: US 8,435,272 B2
(45) Date of Patent: May 7, 2013

(54) CLAVICLE NAIL WITH LOCKING END CAP

(75) Inventors: Christopher P. Dougherty, Bentonville, AR (US); Kevin J. Gallen, Naples, FL (US); Donald K. Shuler, Naples, FL (US)

(73) Assignee: Arthrex, Inc., Naples, FL (US)

( * ) Notice: Subject to any disclaimer, the term of this patent is extended or adjusted under 35 U.S.C. 154(b) by 461 days.

(21) Appl. No.: 12/756,674

(22) Filed: Apr. 8, 2010

(65) Prior Publication Data

US 2010/0262197 A1  Oct. 14, 2010

Related U.S. Application Data

(60) Provisional application No. 61/168,125, filed on Apr. 9, 2009.

(51) Int. Cl.
*A61B 17/86* (2006.01)
*A61F 2/08* (2006.01)

(52) U.S. Cl.
USPC ........................................................ 606/329

(58) Field of Classification Search .................. 606/283, 606/284, 286, 287, 289, 291, 62, 64, 66, 606/65, 67, 300, 329
See application file for complete search history.

(56) References Cited

U.S. PATENT DOCUMENTS

| | | | | |
|---|---|---|---|---|
| 5,653,709 A | * | 8/1997 | Frigg | 606/64 |
| 6,270,499 B1 | * | 8/2001 | Leu et al. | 606/64 |
| 6,648,889 B2 | * | 11/2003 | Bramlet et al. | 606/62 |
| 2008/0221574 A1 | | 9/2008 | Cavallazzi et al. | |

FOREIGN PATENT DOCUMENTS

| | | |
|---|---|---|
| WO | WO 2008/134264 A1 | 11/2008 |
| WO | WO 2009/045751 A1 | 4/2009 |

OTHER PUBLICATIONS

"Rockwood Clavicle Pin" Surgical Technique; DePuy Int'l Limited, Leeds, UK. Nov. 2005.
A. Frigg, MD; "Intramedullary Nailing of Clavicular Midshaft Fractures With the Titanium Elastic Nail"; *The American Journal of Sports Medicine*; Dec. 31, 2008; pp. 1-8.

* cited by examiner

*Primary Examiner* — Anu Ramana
(74) *Attorney, Agent, or Firm* — Dickstein Shapiro LLP

(57) ABSTRACT

A device for reducing migration of a pin of an intramedullary fixation device, especially to reduce migration of a clavicle pin introduced in the medullary canal of the clavicle to fix a fractured clavicle bone. A clavicle nail with a curved tip is inserted within the medullary canal of the clavicle. The back end of the nail that extends out of the clavicle is provided with indentations or grooves. The back end of the nail is received in a hollow cavity of a cap, which locks onto the indentations or grooves of the nail. A screw is placed through an eyelet of the cap and turned into the clavicle to secure the cap to the clavicle. As a result, the nail is fixed within the medullary canal and undesirable migration of the pin within the medullary canal is reduced.

20 Claims, 8 Drawing Sheets

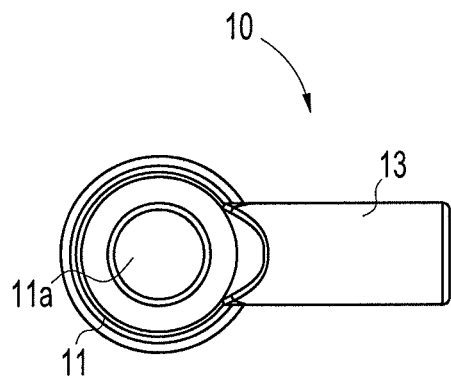 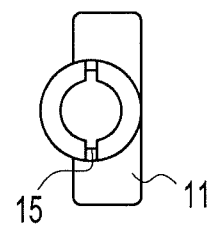
FIG. 2(a)   FIG. 2(b)
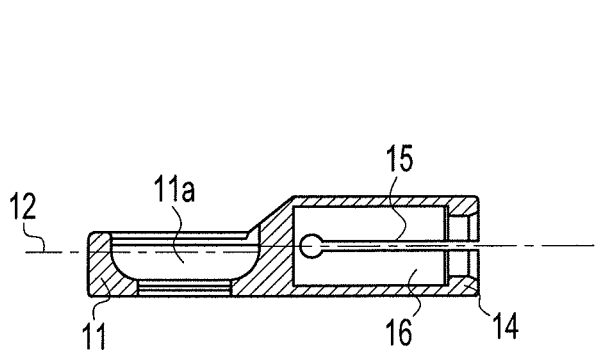 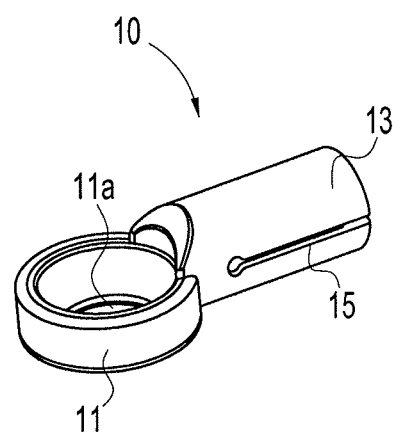
FIG. 2(c)   FIG. 2(d)

CLAVICLE NAIL WITH LOCKING END CAP

CROSS-REFERENCE TO RELATED APPLICATIONS

This application claims the benefit of U.S. Provisional Application No. 61/168,125, filed on Apr. 9, 2009, the entire disclosure of which is incorporated by reference herein.

FIELD OF THE INVENTION

The present invention relates to methods and apparatus for surgical procedures and, more particularly, to a locking clavicular device for securing a fracture nail in the collarbone.

BACKGROUND OF THE INVENTION

Clavicle fractures (also known as broken collarbones) are a common injury. For a long time, the treatment of a clavicle fracture has been simply conservative, non-surgical care (non-operative treatment). Over the last few years, however, various devices such as plates, screws and pins have been developed to aid in the operative treatment of clavicle fractures, reducing the chronic pain, weakness and high nonunion rate typically associated with the non-operative treatment of the clavicle fractures.

For example, clavicle plates have been developed to fix broken collarbones by means of a metal plate placed on top of the broken bone and secured in place with screws through the bone. Similarly, intramedullary fixation devices (which have been used primarily for long bones of the legs and arms) have been also developed for clavicle fractures. Pin fixation within the medullary canal of a broken clavicle is often associated, however, with undesirable migration of the pin within the medullary canal.

Accordingly, an intramedullary fixation device designed specifically for repairing broken collarbones and for holding the fracture nail in place in the collarbone (without medial and lateral movement) is needed.

SUMMARY OF THE INVENTION

The present invention provides a fixation assembly for repairing clavicle (collarbone) fractures. The clavicle fixation assembly of the present invention includes a clavicle end cap (terminal button or terminal cap) configured to securely capture and retain a fracture nail. The end cap is provided with a retaining device and a clavicular nail receptor (locking mechanism). The retaining device has a through opening to allow a fixation device (for example, a screw) to be inserted through the opening and into the broken clavicle to secure the clavicle fixation assembly to the broken clavicle.

The clavicular nail may be provided in incremental diameters between about 1.5 mm to about 3.5 mm. The size chosen is based upon the internal diameter of the patient's intramedullary canal. The nail is designed with a plurality of circumferential grooves or indentations on one end which will mate with the nail receptor of the end cap. The clavicular nail receptor (locking mechanism) of the end cap is designed with a body (having a cylindrical configuration, for example) provided with a cavity extending partially therethrough. The cavity receives an end of the fracture nail and securely retains the captured fracture nail. To aid in the capturing and retention of the fracture nail, the body of the clavicular nail receptor is provided with a plurality of slots that extend about parallel to the longitudinal axis of the end cap. The slots allow the body of the end cap to "spring" open or flare open when the fracture nail is pressed into the open end of the end cap. After the fracture nail is advanced into the cavity of the end cap, the end cap returns to the initial diameter, and securely captures the fracture nail within one of the grooves in the fracture nail. By providing the slots within the body of the end cap, the nail receptor prohibits any lateral and/or medial movement of the captured fracture nail and prevents both lateral and medial migration of the nail, improving therefore the overall success of the fracture repair and preventing possible physiological damage from an internal loose body.

Also provided is an apparatus for surgery including a nail for insertion into a bone having a distal end and a proximal end, the nail having an indentation near the proximal end. The apparatus further includes a retaining device having a circular cross-section with a proximal end and a distal end and a cavity extending from the distal end toward the proximal end, the cavity capable of receiving the proximal end of the nail, the device further having an opening between an inner portion of the cavity and an outer surface of the device, the opening extending from the distal end toward the proximal end of the device. Also the apparatus has a locking mechanism coupled to the distal end of the device, the locking mechanism having a hole that extends through the mechanism and a fastener that extends through the hole of the mechanism to secure the mechanism to the bone.

The present invention also provides a method of repair of a clavicle fracture. The method of clavicle repair of the present invention comprises inter alia the steps of: (i) providing a clavicle fixation assembly that includes a clavicle end cap (terminal button or terminal cap) configured to securely capture and retain a fracture nail, the end cap including a retaining device and a clavicular nail receptor (locking mechanism); (ii) inserting the clavicular fracture nail into the broken clavicle until pieces of the broken clavicle are secured adjacent one another; (iii) cutting off (or shortening) the clavicle nail to the proper length based upon the patient's bone length; (iv) securing the clavicular nail receptor of the end cap (terminal button or terminal cap) at an end of the fracture nail that extends from the clavicle; and (v) inserting a fixation device (for example, a screw or fastener) through an opening of the retaining device of the end cap, and securing the fixation device to the broken clavicle.

Also provided is a method of surgery that includes providing a retaining device having a circular cross-section with a proximal end and a distal end and a cavity extending from the distal end toward the proximal end, the device having an opening between an inner portion of the cavity and an outer surface of the device, the opening extending from the distal end toward the proximal end of the device. The method further involves providing a locking mechanism coupled to the proximal end of the device, the mechanism having a hole that extends through the mechanism and providing a nail having a distal end and a proximal end and an indentation near the proximal end. Further including inserting the distal end of the nail into a bone, inserting the proximal end of the nail into the cavity of the device and inserting a fastener through the hole of the mechanism and into the bone to secure the mechanism to the bone.

Other features and advantages of the present invention will become apparent from the following description of the invention, which refers to the accompanying drawing.

BRIEF DESCRIPTION OF THE DRAWINGS

FIGS. 2(*a*), (*b*), (*c*), and (*d*) illustrates various views of the end cap (terminal button or terminal cap) of the assembly of FIG. 1.

DETAILED DESCRIPTION OF THE PREFERRED EMBODIMENT

Figure 1A:
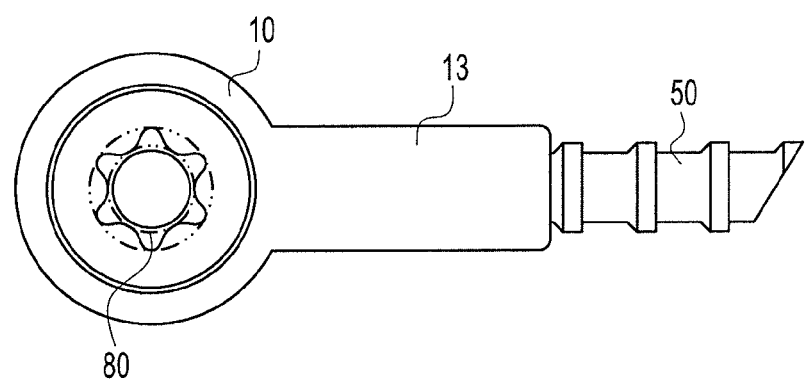
FIGS. 1(a) and (b) illustrates a top view and a cross-sectional view of a clavicle nail assembly of the present invention.

In the following detailed description, reference is made to a specific embodiment in which the invention may be practiced. This embodiment is described with sufficient detail to enable those skilled in the art to practice the invention and it is to be understood that other embodiments may be employed, and that structural and logical changes may be made without departing from the spirit or scope of the present invention.

The present invention provides a fixation assembly for fixing clavicle (collarbone) fractures. The clavicle fixation assembly of the present invention includes a clavicle end cap (terminal button or terminal cap) configured to securely capture and retain a fracture nail. The end cap is provided with a retaining device and a clavicular nail receptor.

The retaining device is provided with a through opening to allow a fixation device (for example, a screw or fastener) to be inserted through the opening and into the broken clavicle to secure the clavicle fixation assembly to the broken clavicle.

The clavicular nail receptor (locking mechanism) of the end cap is designed with a body (having a cylindrical configuration, for example) provided with a cavity extending partially therethrough. The cavity receives an end of the fracture nail and securely retains the captured fracture nail. To aid in the capturing and retention of the fracture nail, the body of the clavicular nail receptor is provided with a plurality of slots that run about parallel to the longitudinal axis of the end cap. The slots allow the body of the end cap to "spring" open or flare open when the fracture nail is pressed into the open end of the end cap. After the fracture nail is advanced into the cavity of the end cap, the end cap returns to the initial diameter and securely captures the fracture nail within one of the grooves in the fracture nail. By providing the slots within the body of the end cap, the nail receptor prohibits any lateral and/or medial movement of the captured fracture nail and prevents both lateral and medial migration of the nail improving the overall success of the fracture repair.

The present invention also provides a method of repair of a clavicle fracture. The method of clavicle repair of the present invention will be described in more detail with reference to FIGS. 6-9. In an exemplary embodiment only, the method of the present invention comprises inter alia the steps of: (i) providing a retaining device having a circular cross-section with a proximal end and a distal end and a cavity extending from the distal end toward the proximal end, the device having an opening between an inner portion of the cavity and an outer surface of the device, the opening extending from the distal end toward the proximal end of the device; (ii) providing a locking mechanism coupled to the proximal end of the device, the mechanism having a hole that extends through the mechanism; (iii) providing a nail having a distal end and a proximal end and an indentation near the proximal end; (iv) inserting the distal end of the nail into a bone; (v) inserting the proximal end of the nail into the cavity of the device; and (vi) inserting a fastener through the hole of the mechanism and into the bone to secure the mechanism to the bone.

Referring now to the drawings, where like elements are designated by like reference numerals, FIGS. 1-5 illustrate various components of clavicle fixation assembly 100 of the present invention. As shown in the drawings, clavicle fixation assembly 100 includes a clavicle end cap (terminal button or terminal cap) 10 configured to securely capture and retain a fracture nail 50. A fixation device 80 (for example, a screw or a fastener) is inserted through an opening of end cap (terminal button or terminal cap) 10 and into the broken clavicle, to secure the clavicle fixation assembly 100 to the broken clavicle.

Figure 1B:
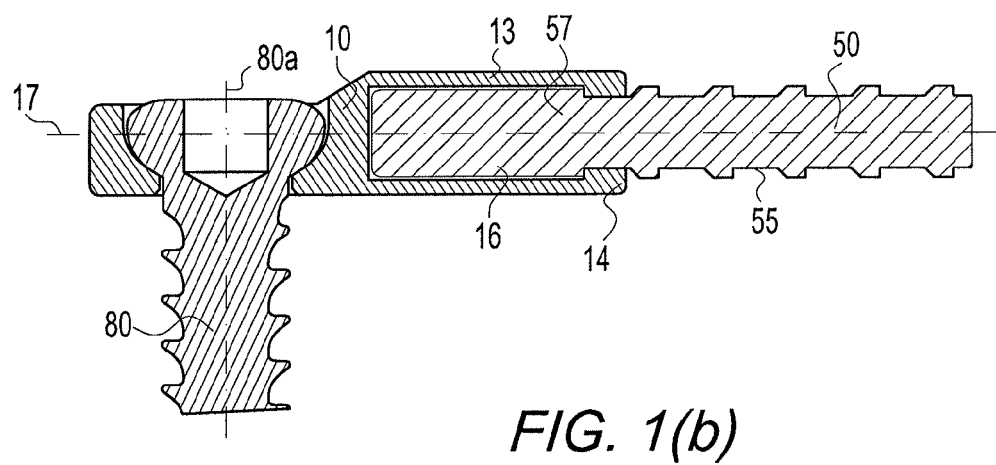

FIGS. 2(*a*)-(*d*) illustrate various views of the end cap (terminal button or terminal cap) 10 of the assembly 100 of FIG. 1. End cap 10 is provided with a retaining device 11 and a clavicular nail receptor 13. As described below, the clavicular nail receptor 13 acts as a locking mechanism for capturing and securely preventing movement of the fracture nail 50 in at least a medial and lateral direction.

As shown in FIGS. 2(*a*)-(*d*), clavicular nail receptor 13 (locking mechanism 13) is provided with a body (having a cylindrical configuration, for example) defining a cavity 16 extending partially therethrough. The cavity 16 has an annular protrusion 14 that extends toward the center of the cavity 16. The annular protrusion 14 has a circumference that is smaller than the circumference of the cavity 16. The circumference of the protrusion 14 is approximately equal to the circumference of the indentations 55 on the nail 50 and the width of the protrusion 14 is approximately equal to the width of the indentations 55. The indentations 55 haves a smaller circumference then the circumference of the nail 50. Also, the circumference of the cavity 16 is approximately equal to the circumference of the nail 50.

The cavity 16 receives an end 57 of the fracture nail 50 and securely retains the captured fracture nail (FIGS. 1(*a*) and 1(*b*)). To aid in the capturing and retention of the fracture nail 50, the body of the clavicular nail receptor 13 is provided with a plurality of slots 15 that extend about parallel to the longitudinal axis 12 of the end cap 10. The slots 15 allow the body of the end cap to "spring" open or flare open when the fracture nail 50 is pressed into the open end of cavity 16 of the end cap 10.

The body of the end cap flares open because the circumference of the protrusion 14 is smaller than the circumference of the nail 50. So as the nail 50 is pressed against the protrusion 14, the body flares open to allow the nail 50 to pass into the cavity 16. After the fracture nail 50 is advanced into the cavity 16 of the end cap 13 and the protrusion 14 rest within at least one of the grooves or indentations 55 (FIG. 3(*b*)) the end cap returns to its initial circumference, thereby securely capturing the fracture nail 50 within the cavity 16. Thus, by providing the slots 15 within the body of the end cap the nail receptor 13 may prevent both lateral and medial migration of the nail 50, thereby improving the overall success of the fracture repair.

FIGS. 2(*a*)-(*d*) also illustrate retaining device 11 of end cap 10. Retaining device 11 is coupled to an end of clavicular nail receptor 13 and is configured to secure a locking or fixation device 80. In an exemplary embodiment only, the retaining device 11 is generally cylindrical and has an opening 11*a* extending therethrough. Opening 11*a* is configured to receive fixation device (screw) 80, as shown in FIGS. 1(*a*) and 1(*b*), for example. Fixation device (screw) 80 is inserted through opening 11*a* and then is secured into the broken clavicle, thereby affixing the locking assembly 100 to the broken clavicle. In an exemplary embodiment, fixation device (screw) 80 is inserted through opening 11*a* so that the longitudinal axis 80*a* of the fixation device (screw) 80 is about perpendicular to the longitudinal axis 17 of the clavicular nail receptor 13.

Figure 3A:
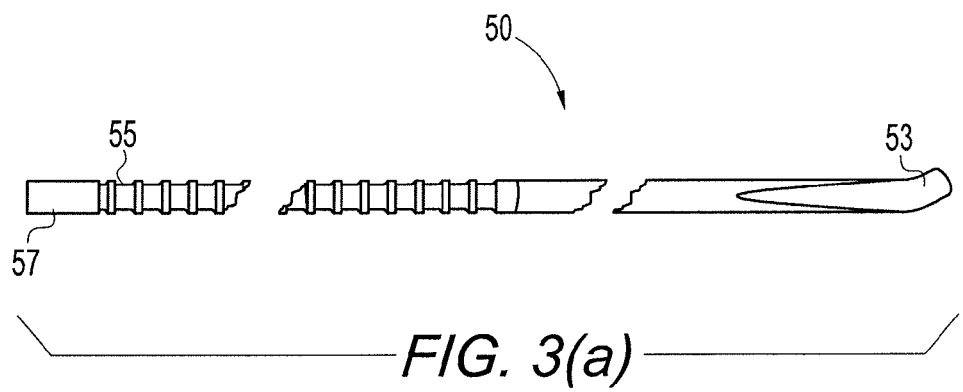
FIGS. 3(*a*) and (*b*) illustrates various views of the fracture nail of the assembly of FIG. 1.
Figure 3B:
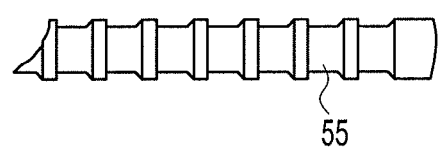
Figure 4:
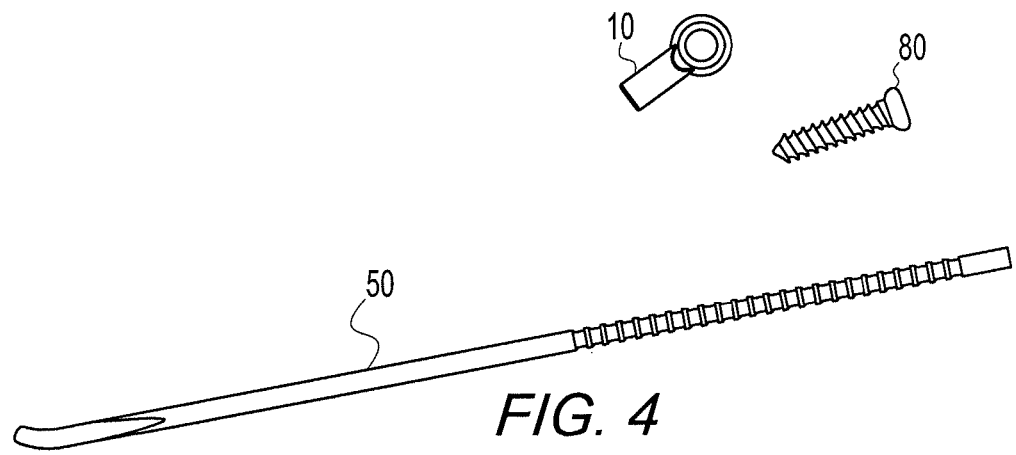
FIG. 4 illustrates the distinct parts of the assembly of FIG. 1.
Figure 5:
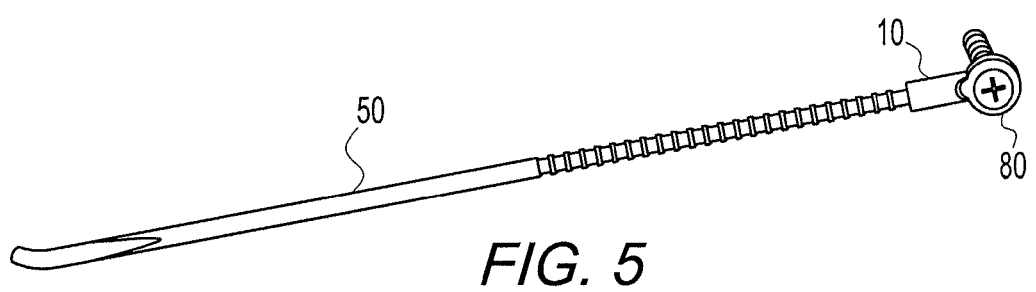
FIG. 5 illustrates another view of the assembly of FIG. 1.

FIGS. 3(*a*) and 3(*b*) illustrate various views of the fracture nail 50 employed with clavicle assembly 100 of the present invention. End 53 of the nail 50 may be provided with a bent region (as shown in FIG. 3(*a*)) to facilitate entry of the nail into the clavicle. Specifically, the bent region 53 enables the end of the clavicle nail to tunnel into the clavicle by twisting the nail, thereby easing the insertion of the nail. Preferably, nail 50 is inserted into the clavicle until broken pieces of the clavicle are held securely adjacent one another via nail 50. A second end 57 of nail 50 remains exposed at the location where nail 50 was inserted into the clavicle. The second end 57 is captured and secured within cavity 16 of the clavicular nail receptor 13 (locking mechanism 13). If the second end 57 protrudes too far past the entry hole into the broken clavicle, the nail may be cut to the proper length anywhere within the grooved or indented area 55 of the nail so that the nail may still be captured within the cavity 16 of the clavicle nail receptor 13.

The clavicular nail 50 is generally flexible, but rigid in the axial plane, and may be manufactured from biocompatible materials such as titanium or titanium alloy, among many others. The nail 50 is preferably flexible to enable bending to accommodate a shape of the clavicle while being inserted through the clavicle. The nail 50 may also be fabricated from a material having the requisite strength to support the clavicle as the clavicle heals. Nail 50 also has a length and diameter that is sufficient for insertion through the clavicle. It should be understood by one of ordinary skill in the art that the size of nail 50 varies depending on its use and a size of the patient receiving the nail 50.

Figure 6:
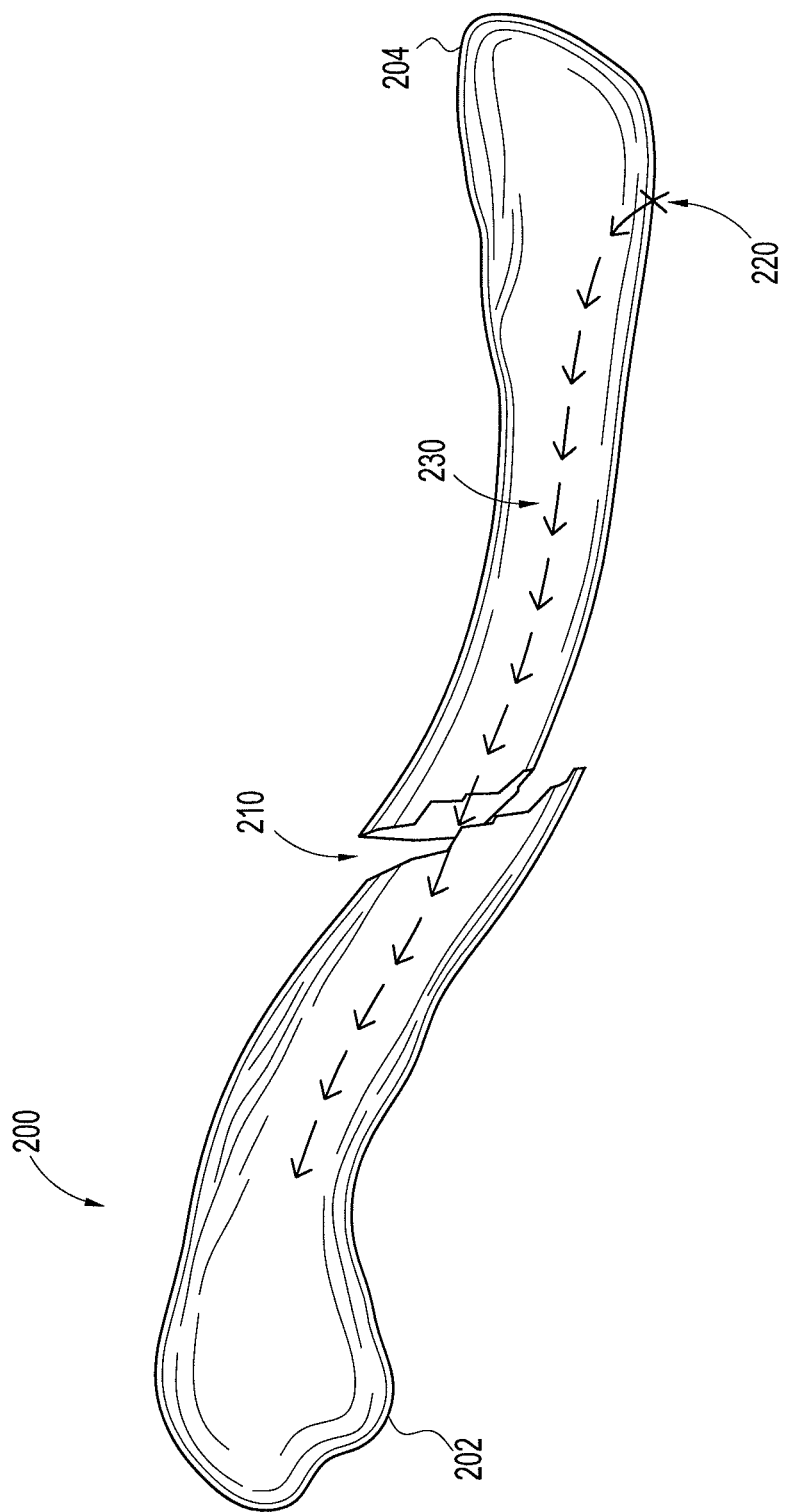
FIG. 6 illustrates a superior view of a broken clavicle bone.

The present invention also provides a method of repair of a clavicle fracture as shown in FIGS. 6-9. FIG. 6 shows a superior view of a clavicle 200 with a lateral end 202 and a medial end 204. The clavicle 200 has a fracture 210. The method of clavicle repair of the present invention is detailed below:

A clavicle fixation assembly 100 is provided that includes a clavicle end cap (terminal button or terminal cap) 10 configured to securely capture and retain a fracture nail 50, the end cap 10 including a retaining device 11 and a clavicular nail receptor (locking mechanism) 13.

The clavicular fracture nail 50 is inserted into the broken clavicle 200 in the insertion point 220 and passes through the clavicle 200 along path 230 (FIG. 6). After the nail 50 passes into the lateral end 202 of the bone, the fracture nail 50 is twisted until fragments of the broken clavicle are secured adjacent one another.

Figure 7:
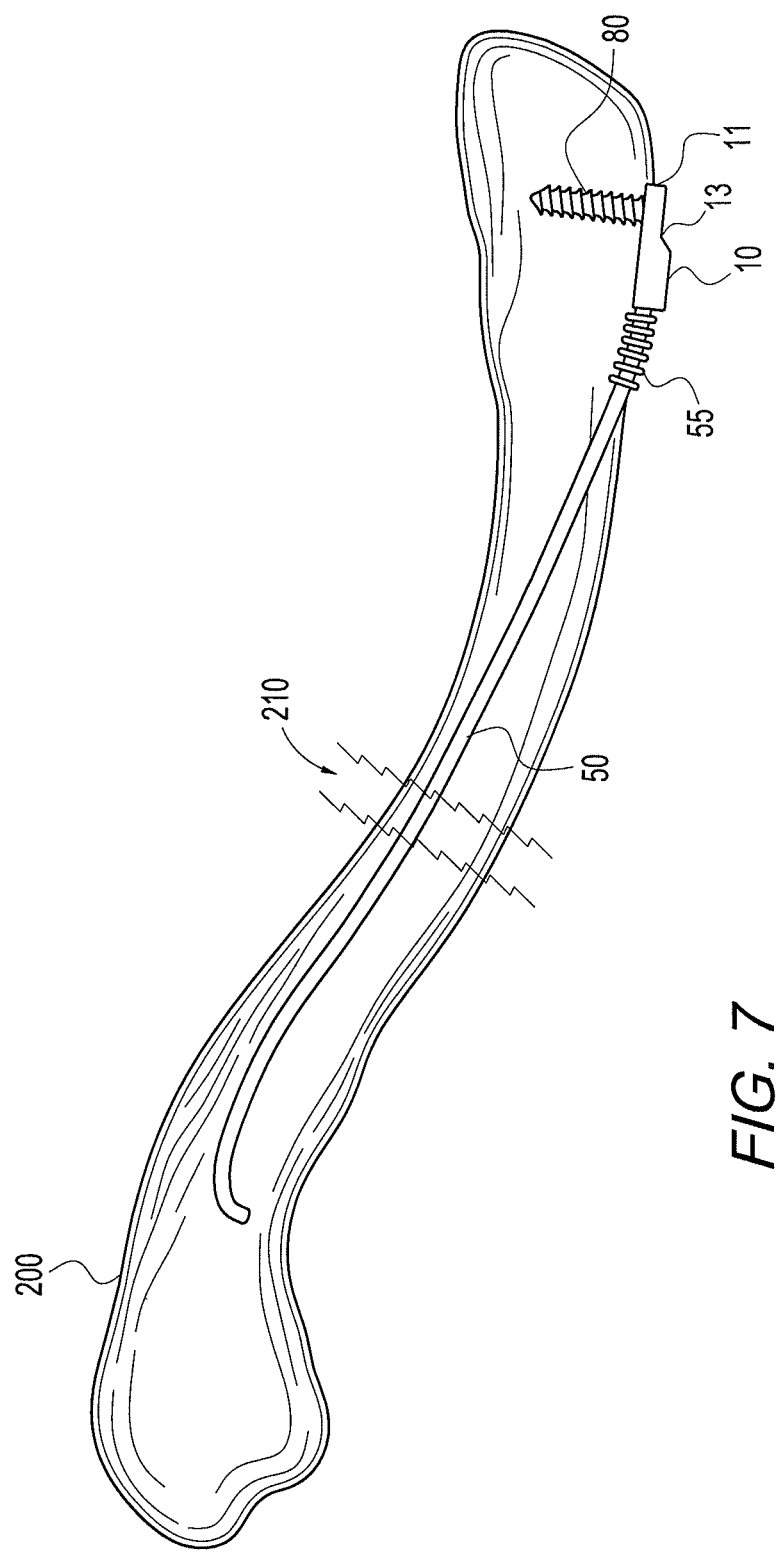
FIG. 7 illustrates a superior view of the assembly of FIG. 1 within a clavicle bone.
Figure 8:
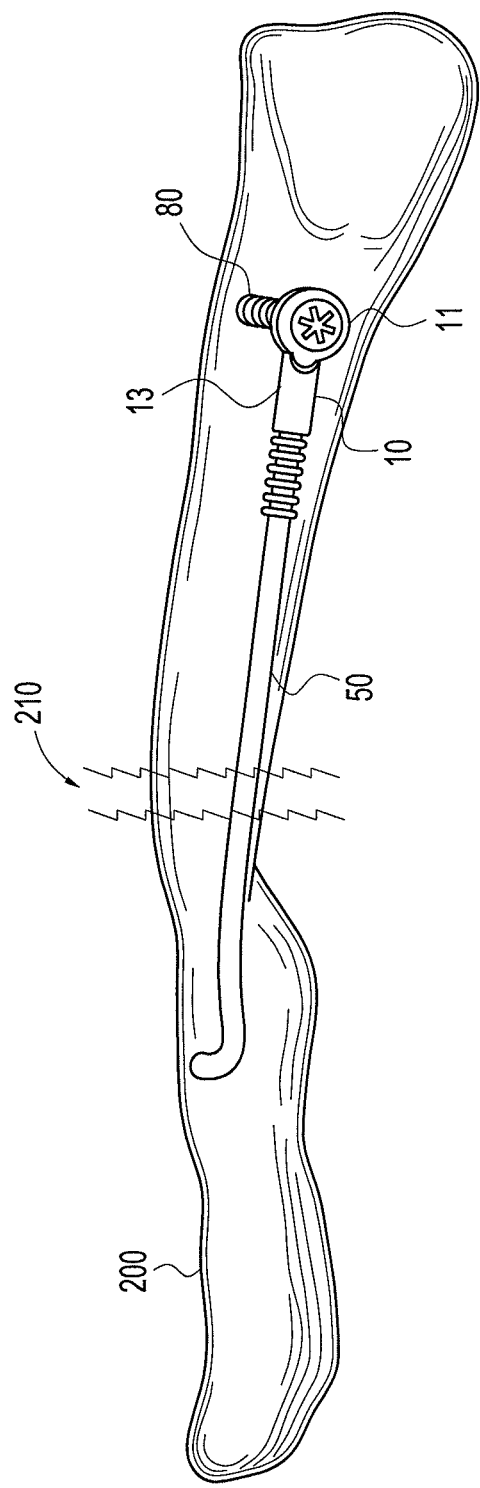
FIG. 8 illustrates an anterior view of the assembly of FIG. 1 within a clavicle bone.
Figure 9:
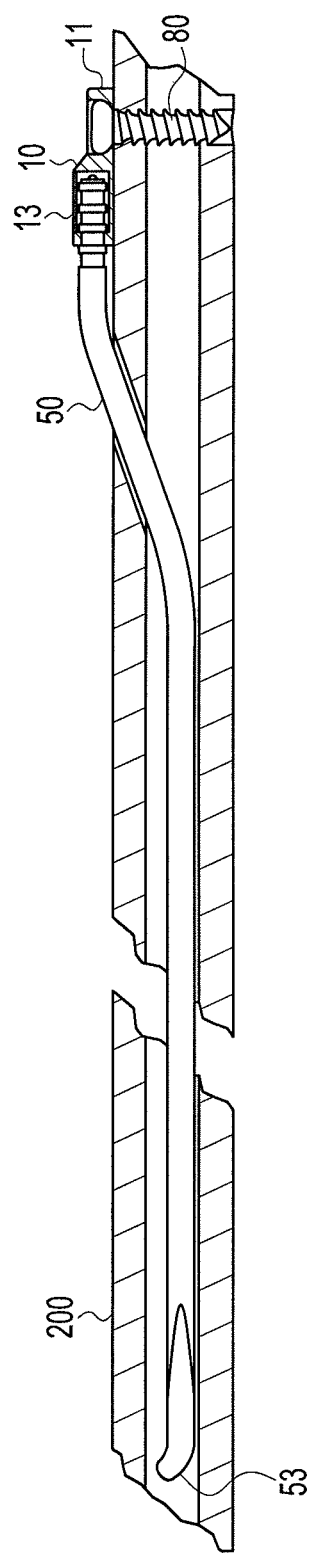
FIG. 9 illustrates a cross-sectional view of the assembly of FIG. 1 within a clavicle bone.

Next, the clavicular nail receptor 13 of the end cap (terminal button or terminal cap) 10 is secured to an end of the fracture nail 50 that extends from the clavicle 200 as shown in FIGS. 7-9.

Next, a fixation device (for example, a screw or a fastener) 80 is inserted through an opening 11*a* of the retaining device 11 of the end cap 10, and the fixation device 100 is secured to the broken clavicle 200 as shown in FIGS. 7-9.

The above description and the drawings illustrate only exemplary and/or preferred embodiments which achieve the objects, features and advantages of the present invention. It is not intended that the present invention be limited to the illustrated embodiments.

What is claimed as new and desired to be protected by Letters Patent of the United States is:

1. A method of surgery comprising:
    providing a fixation assembly comprising an end cap configured to securely capture and retain a fracture nail, the end cap being provided with a retaining device and a nail receptor, the nail receptor comprising a body defining at a first end a cavity extending partially therethrough for receiving a proximal end of the nail;
    providing a nail having a distal end and a proximal end and an indentation near the proximal end;
    inserting the distal end of the nail into a broken bone;
    inserting the proximal end of the nail into the cavity of the nail receptor so that the body of the nail receptor flares open when the proximal end of the nail is inserted into the cavity; and
    inserting a fastener through an opening of the retaining device and into the bone to secure the fixation assembly to the bone.

2. The method of claim 1, wherein the indentation extends circumferentially around the nail.

3. The method of claim 2, wherein the body of the nail receptor has an annular protrusion at the first end that extends into the cavity.

4. The method of claim 3, wherein the nail is inserted into the cavity so that the protrusion rests within the indentation on the nail thereby restricting lateral or medial motion of the nail.

5. The method of claim 1, wherein the nail has a curvature on a distal end.

6. The method of claim 1, wherein the distal end of the nail is inserted into a broken clavicle.

7. The method of claim 1, wherein the nail receptor has a slot that is u-shaped.

8. The method of claim 7, wherein the nail receptor has a second u-shaped slot.

9. The method of claim 7, wherein the slot extends about parallel to a longitudinal axis of the nail receptor.

10. The method of claim 1, further comprising cutting the nail to an appropriate size.

11. An apparatus for surgery comprising:
    a nail for insertion into a bone having a distal end and a proximal end, the nail having an indentation near the proximal end;
    an end cap comprising a retaining device and a nail receptor, the nail receptor comprising a body defining at a first end a cavity extending partially therethrough for receiving the proximal end of the nail and a plurality of slots extending from an open end of the cavity toward a second end of the body and about parallel to a longitudinal axis of the body so that the body flares open at the first end when the proximal end of the nail is pressed into the open end of the cavity, the retaining device being coupled to a second end of the body of the nail receptor, the retaining device having a hole that extends through the retaining device; and
    a fastener that extends through the hole of the retaining device to secure the retaining device to the bone.

12. The apparatus of claim 11, wherein the nail has a curvature on the distal end.

13. The apparatus of claim 11, wherein the distal end of the nail is configured to be inserted into a broken clavicle.

14. The apparatus of claim 11, wherein the indentation extends circumferentially around the nail.

15. The apparatus of claim 14, wherein the body has an annular protrusion at the first end that extends into the opening.

16. The apparatus of claim 15, wherein the body receives the nail in the cavity so that the protrusion rests within the indentation on the nail thereby restricting lateral or medial motion of the nail.

17. The apparatus of claim 15, wherein a circumference of the annular protrusion is smaller than a circumference of the nail.

18. The apparatus of claim 15, wherein a circumference of the annular protrusion is approximately equal to a circumference of the indentation on the nail.

19. The apparatus of claim 11, wherein the slots are u-shaped.

20. The apparatus of claim 11, wherein a longitudinal axis of the fastener is about perpendicular to a longitudinal axis of the retaining device.

\* \* \* \* \*